(12) United States Patent
Boettcher et al.

(10) Patent No.: US 10,363,528 B2
(45) Date of Patent: Jul. 30, 2019

(54) MIXING AND THAWING DEVICE

(71) Applicant: Sartorius Stedim Biotech GmbH, Goettingen (DE)

(72) Inventors: Lars Boettcher, Melsungen (DE); Marcel Roell, Tagelswangen (CH); Martin Dahlberg, Bovenden (DE); Swen Weitemeier, Adelebsen (DE)

(73) Assignee: Sartorius Stedim Biotech GmbH (DE)

( * ) Notice: Subject to any disclaimer, the term of this patent is extended or adjusted under 35 U.S.C. 154(b) by 147 days.

(21) Appl. No.: 15/125,594

(22) PCT Filed: Apr. 16, 2015

(86) PCT No.: PCT/EP2015/058315
§ 371 (c)(1),
(2) Date: Sep. 13, 2016

(87) PCT Pub. No.: WO2015/158852
PCT Pub. Date: Oct. 22, 2015

(65) Prior Publication Data
US 2017/0036181 A1 Feb. 9, 2017

(30) Foreign Application Priority Data
Apr. 16, 2014 (DE) .................. 10 2014 105 472

(51) Int. Cl.
*B01F 11/00* (2006.01)
*C12M 1/34* (2006.01)
(Continued)

(52) U.S. Cl.
CPC ........... *B01F 11/0008* (2013.01); *A61M 5/44* (2013.01); *A61M 5/445* (2013.01);
(Continued)

(58) Field of Classification Search
CPC ...... C12M 23/14; C12M 41/12; C12M 27/16; B01L 2300/1838; B01L 2300/1844; A61M 1/025
(Continued)

(56) References Cited

U.S. PATENT DOCUMENTS

| | | | |
|---|---|---|---|
| 2,845,929 A * | 8/1958 | Strumia | A61M 1/02 366/144 |
| 3,480,015 A * | 11/1969 | Gonzalez | F25B 21/02 392/470 |
| 4,473,739 A | 9/1984 | Scheiwe et al. | |
| 4,708,938 A | 11/1987 | Hickinbotham | |
| 4,801,777 A | 1/1989 | Auerbach | |
| 5,902,618 A | 5/1999 | Haasis, Jr. | |

(Continued)

FOREIGN PATENT DOCUMENTS

DE 35 15 615 10/1985
DE 37 30 981 3/1989
(Continued)

OTHER PUBLICATIONS

International Preliminary Report for Application No. PCT/EP2015/058315 dated Apr. 16, 2015.
International Search Report.

*Primary Examiner* — Tony G Soohoo
*Assistant Examiner* — Elizabeth Insler
(74) *Attorney, Agent, or Firm* — Gerald E. Hespos; Michael J. Porco; Matthew T. Hespos

(57) ABSTRACT

A mixing and thawing device (1) has a rocker drive (2) and a bag holder (3) for holding a bag (7). The bag holder (3) has a base part (8) and a lid part (9) that enclose a holding space (10) for the bag (7). A heating element (11) is arranged in the base part (8). Thus, the holding space (10) is designed as a heat-insulating closed chamber. Interconnected intermediate spaces (14, 15) are arranged between the bag (7) and the base part (8) and between the bag (7) and the lid part (9). One or more flow generators (16) are provided to generate a circulating fluid flow (17).

14 Claims, 6 Drawing Sheets

(51) Int. Cl.
*C12M 1/00* (2006.01)
*C12M 3/06* (2006.01)
*B01F 15/00* (2006.01)
*B01F 15/06* (2006.01)
*A61M 5/44* (2006.01)

(52) U.S. Cl.
CPC .... *B01F 15/0085* (2013.01); *B01F 15/00396* (2013.01); *B01F 15/065* (2013.01); *C12M 23/14* (2013.01); *C12M 27/16* (2013.01); *C12M 41/12* (2013.01); *A61M 2205/362* (2013.01); *B01F 2015/062* (2013.01); *B01F 2215/0073* (2013.01)

(58) Field of Classification Search
USPC ......................................................... 366/145
See application file for complete search history.

(56) References Cited

U.S. PATENT DOCUMENTS

| | | | |
|---|---|---|---|
| 8,012,416 B2* | 9/2011 | Kuzyk | H05B 3/82 392/443 |
| 8,058,588 B2* | 11/2011 | Gagas | A47J 36/2483 219/400 |
| 8,129,178 B2 | 3/2012 | Houtzager et al. | |
| 2012/0100605 A1 | 4/2012 | Kauling et al. | |

FOREIGN PATENT DOCUMENTS

| | | |
|---|---|---|
| DE | 42 30 774 | 3/1994 |
| DE | 197 26 625 | 12/1998 |
| DE | 197 52 578 | 6/1999 |
| DE | 10 2009 019 697 | 11/2010 |
| JP | 2007-61245 | 3/2007 |
| WO | 2010/123205 | 10/2010 |

* cited by examiner

MIXING AND THAWING DEVICE

BACKGROUND

1. Field of the Invention

The invention relates to a mixing and thawing device consisting of a rocker drive and a bag holder for holding a bag, wherein the bag holder has a base part and a lid part which enclose a holding space for the bag, a heating element being arranged in the base part.

2. Description of the Related Art

A mixing device is known from the brochure for the BIOSTAT® RM produced by the company Sartorius Stedim Biotech GmbH, with a rocker drive and bag holder to hold a flexible bioreactor designed as a bag. The bag holder consists of a base part and a lid part, which enclose a holding space for the bag, whereby a temperature-controlled heating pad is arranged within the base part. This device has a rocking platform, also known as a "rocker," that serves as a bag holder for single-use bioreactors. The platform's wave-based mixing process uses mechanical energy to achieve homogeneous intermixture of cells. The necessary energy is supplied by the low-shear, rocking motion of the flexible bioreactor (CultiBag RM) fastened to the rocker. This type of motion is gentle on cells and ensures a homogeneous cell distribution within the cultivation medium, whereby the surface of the medium is continually renewed, without bubble formation.

This device, which has basically proven itself, is not intended for use as a thawing device. There is a very high volume of air in the bag holder and this acts as a relatively poor heat conductor. Additionally, condensate water that forms during a thawing process could disrupt the thawing process.

The problem that the present invention seeks to solve is to further develop a device such that it is suitable for use as both a mixing device as well as a thawing device for fluid media arranged in a bag.

As used here, a fluid medium generally refers to a material that is in a fluid state or which can be changed to a fluid state after warming it. The fluid medium can contain substances. These can comprise biological material. Such contained substances can be buffer substances, ions, acids, bases, organic solvents or similar. It is also possible for the fluid medium to not contain any other substances. Frozen water is an example of a fluid medium that can be changed to a fluid state by warming it.

SUMMARY

This problem is solved in that the holding space is designed as a heat-insulating closed chamber, in that interconnected intermediate spaces are arranged between the bag and the base part and between the bag and the lid part, and in that a circulating fluid flow can be generated by at least one flow generator.

By means of the heat-insulating closed chamber, the bag containing the medium, which may be frozen, advantageously can be thawed and/or temperature-controlled with relatively little energy. The bag can be arranged directly between the base part and the lid part and/or between a bowl-shaped lower part and a bowl-shaped lid part. Intermediate spaces with reduced volume as compared to the base part and lid part may be formed by the base part and lid part, or by the bowl-shaped lower part and the bowl-shaped upper part. A circulating fluid flow supportive of heating may be produced in the intermediate spaces using one or more flow generators. The flow may be directed over the heating element, for example a heating plate or heating pad.

The heating plate or pad can be operated in a temperature-controlled manner. In principle operation without temperature control is also possible when, for instance, moderate, limited, low or no heat energy is supplied through the heating element, the heating plate and/or heating device.

The bag can be a bioreactor, for example. The device according to the invention, however, serves not only for cell cultivation but also for thawing and/or intermixing any biopharmaceutical products/intermediate products contained in bags, preferably single-use bags. The upper part and lid part, on one hand, and the base part and lower part, on the other, generally only come into contact at certain points. The resulting intermediate spaces thus form, in the broadest sense, a type of flow channel that supports a homogeneous temperature distribution.

The bag can comprise wholly or partly of a flexible material or a rigid material. The bag can be intended for single use or multiple use. The bag can contain a fluid that is in a fluid state at room temperature or which is frozen.

A fluid flow is a moving gaseous (e.g., air, oxygen, nitrogen, noble gas) or fluid medium (e.g., water, aqueous solution).

The one or more flow generator may be a fan and the fluid flow is an air stream. This can be implemented cost-effectively with relatively little outlay.

The holding space may include a lower part adjacent to the base part and an upper part adjacent to the lid part.

The lower part and the upper part may form a protective housing for the bag. This allows the bag along with the protective housing to be relatively easily and reliably placed into, as well as removed from, the bag holder.

The intermediate spaces may comprise a first intermediate space arranged between the lower part and the base part and a second intermediate space arranged between the upper part and the lid part.

The base part may have one or more condensate outlets. The arrangement of a condensate outlet on the base part allows for easy and reliable drainage of condensate that forms during thawing.

The bag may be fastened within the holding space to prevent slippage. Securing against slippage ensures, on one hand, the effectiveness of the mixing process and on the other, a gentle type of motion to homogenize the medium. The medium being mixed is therefore generally intermixed in a gentle and effective manner.

The lid part may be removable from the base part. The removable lid part makes handling considerably more straightforward when inserting and removing the bag, which can be in the form of a container having at least one flexible side (flexible bag).

A heat-conducting gel pad may be arranged on the heating element, facing the bag. On one hand, the heat-conducting gel pad is a better heat conductor than air and on the other, the surface of a flexible bag can lie against it, resulting in good heat conduction.

The gel pad itself may be flexible. Since the heat-conducting gel in the gel pad has a certain viscosity, the gel pad can adapt to the contour of the bag in a form-fitting manner, thereby resulting in good heat transfer.

The gel pad may fasten the bag even more securely in the holding space, thereby further preventing slippage.

The temperature of the heating element may be controlled.

The lower part and/or the upper part may be bowl-shaped. The lower part and/or upper part can also be semi-circular, oval or egg-shaped.

One or more temperature sensors may be arranged within the bag holder. The temperature sensor is particularly advantageous in connection with a control and regulation device for controlling and regulating a thawing and/or mixing process capable of being executed using the mixing and thawing device. Additional appropriate sensors can also be used to control and regulate additional parameters of the mixing and thawing process. In principle, it is also possible to perform a mixing process without heating or temperature-controlling the bag. The mixing process can therefore also be performed without the prior thawing process.

In principle, the device according the invention can also perform a mixing process without heating or temperature-controlling the bag.

Additional features and advantages of the invention are evident from the following special description and the drawings.

DETAILED DESCRIPTION

Figure 1:
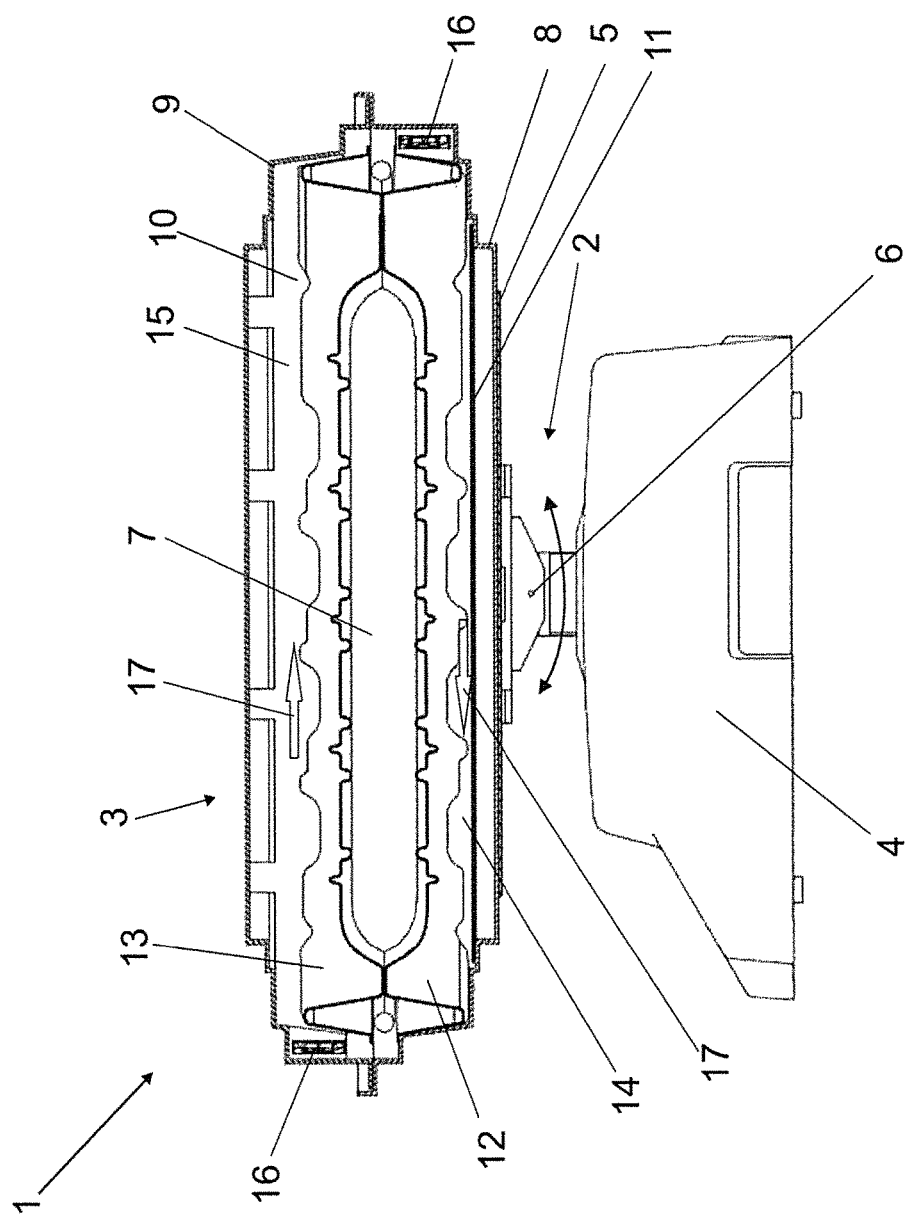
FIG. 1 a lateral, partially cross-sectional view of a mixing and thawing device.
Figure 2:
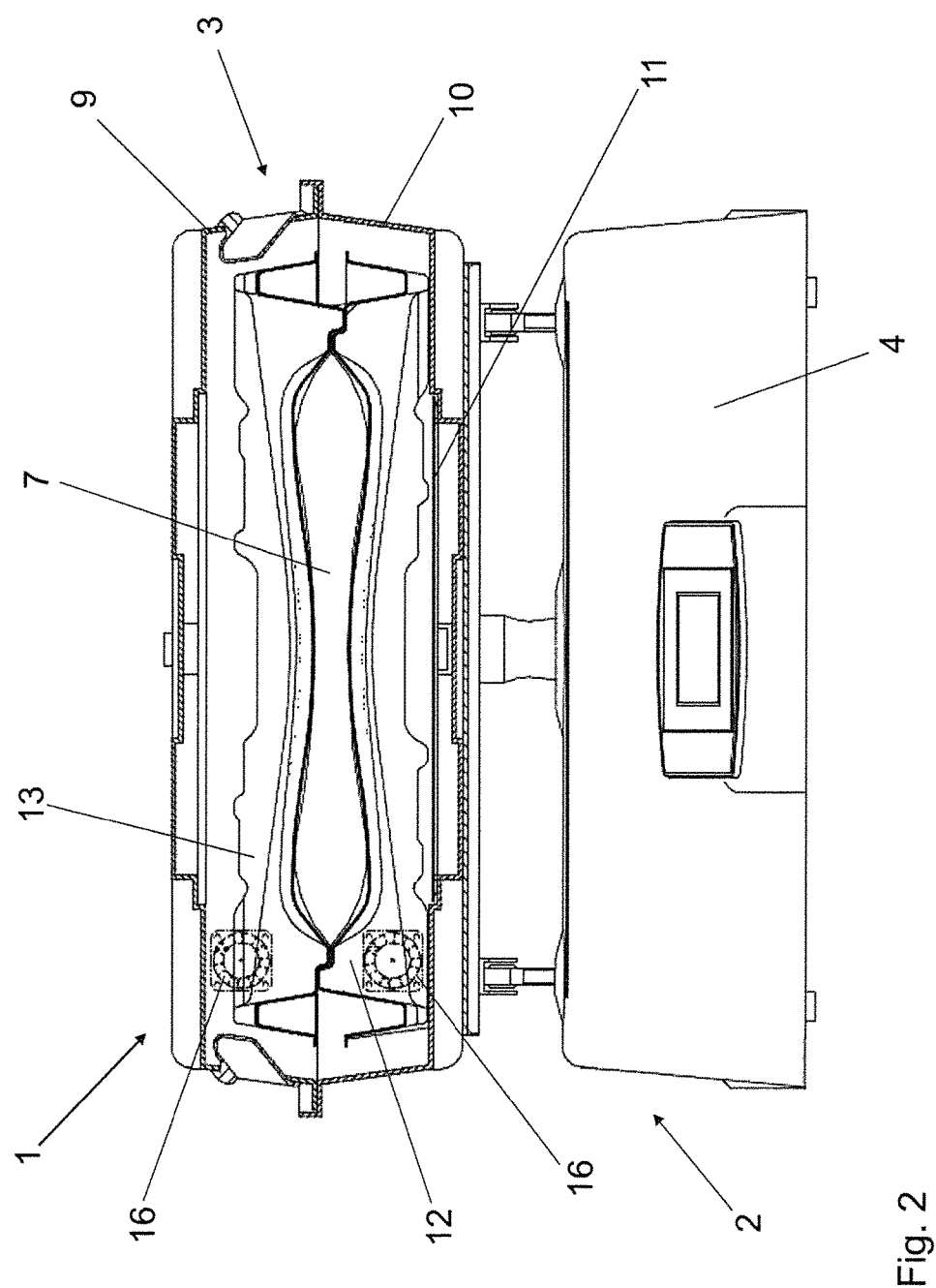
FIG. 2 a frontal, partially cross-sectional view of the mixing and thawing device from FIG. 1, from Direction II.

A mixing and thawing device 1 essentially comprises a rocker drive 2 and a bag holder 3.

The rocker drive 2 comprises, in a manner known, a substructure 4 and a rocker plate 5 that is capable of pivoting about a rocker axis 6 at a programmable frequency and programmable angle.

The bag holder 3 for holding a bioreactor designed as a bag 7 with flexible walls has a base part 8 and a lid part 9 that enclose a holding space 10 for the bag 7. The base part 8 of the bag holder 3 is securely fastened to the rocker plate 5.

A heating pad 11 is arranged within the base part 8 and can also be designed as a flat temperature-controlled plate.

The holding space 10 is designed as a heat-insulating, closed chamber in which the bag 7 is arranged between a bowl-shaped lower part 12 adjacent to the base part 8 and a bowl-shaped upper part 13 adjacent to the lid part 9. A first intermediate space 14 is located between the lower part 12 and the base part 8 while a second intermediate space 15 is located between the upper part 13 and the lid part 9. The intermediate spaces 14, 15 are connected to one another such that a circulating flow 17 (e.g., air stream) can be produced by the flow generator(s) 16 (e.g., fans) (see FIG. 1).

Figure 3:
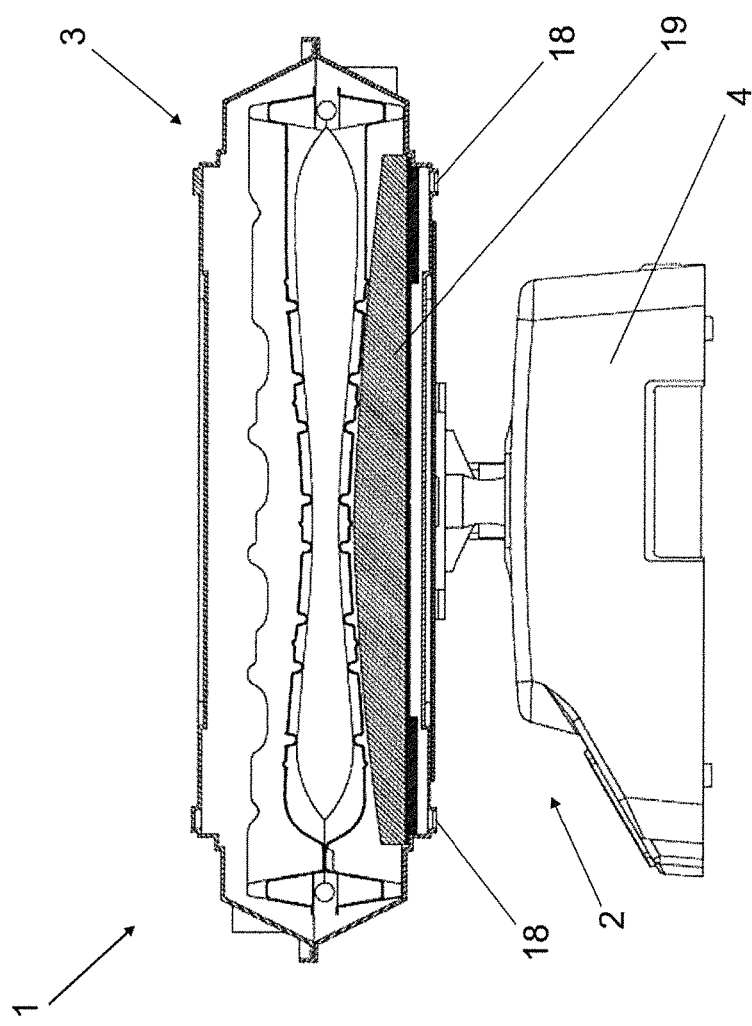
FIG. 3 a lateral, partially cross-sectional view of an additional mixing and thawing device with a heat-conductive gel pad in the bag holder.
Figure 6:
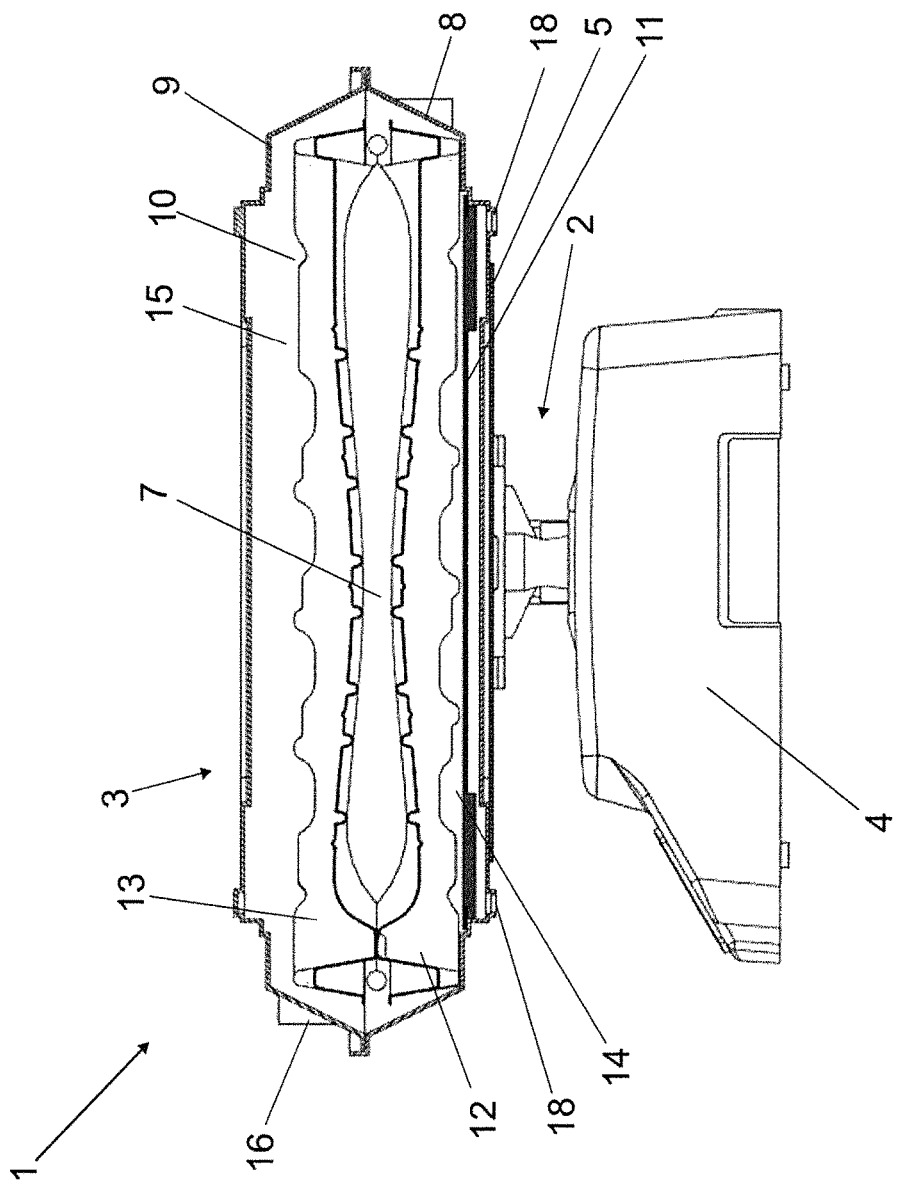
FIG. 6 a lateral, partially cross-sectional view of an additional mixing and thawing device with condensate outlets in the bag holder.

According to the exemplary embodiments of FIGS. 3 and 6, the base part 8 has one or more condensate outlets 18.

Figure 4:
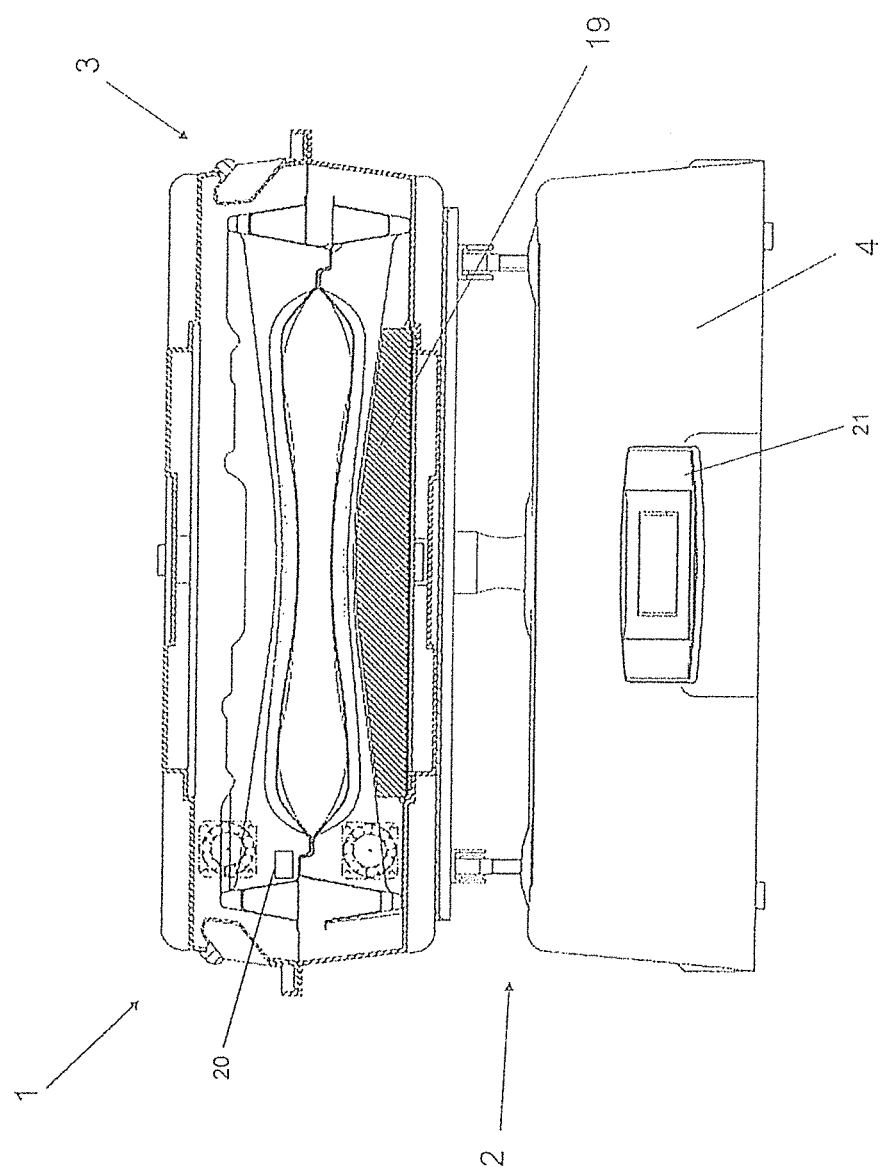
FIG. 4 a frontal, partially cross-sectional view of the mixing and thawing device from FIG. 3, from Direction IV.
Figure 5:
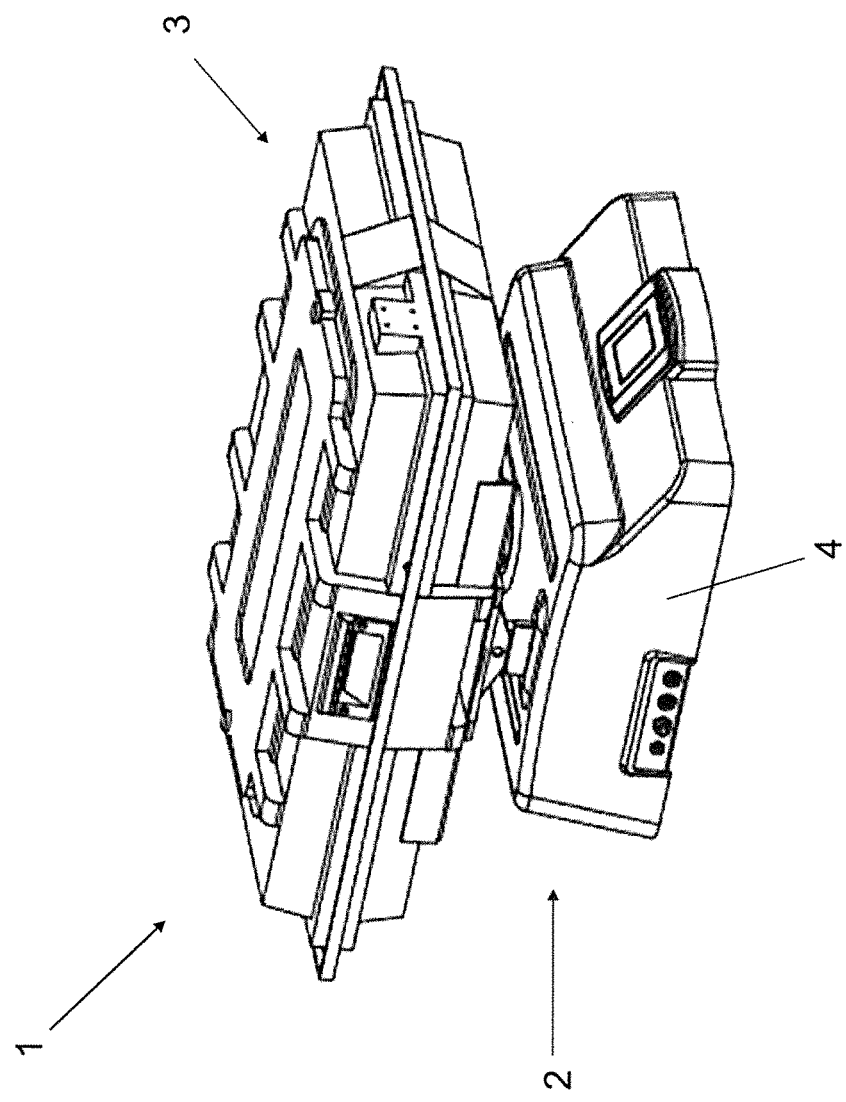
FIG. 5 a spatial representation of the mixing and thawing device from FIG. 1.

According to the exemplary embodiments of FIGS. 3 and 4, a gel pad 19 with good heat conduction is arranged on the heating pad 11, facing the bag 7. The gel bag 19 is flexible.

The mixing and thawing device 1 has one or more temperature sensors 20 within the bag holder 3.

A control and regulation device (21) for controlling and regulating a thawing and/or mixing process to be executed using the mixing and thawing device 1 is arranged within the rocker drive 2, i.e., in its substructure 4.

To insert the bag 7 into the bag holder 3, the lid part 9 with the upper part 13 is removed from the base part 8 with the lower part 12. The bag 7 is then inserted into the base part 8 with the lower part 12 and the upper part 13, and the lid part 9 is placed onto the base part 8 and locked.

Afterwards, a thawing process, and subsequently a mixing process, can be performed.

It is evidently also possible to perform a mixing process directly and without a prior thawing process.

Of course, the embodiments discussed in the specific description and shown in the figures are merely illustrative exemplary embodiments of the present invention. In light of this disclosure, a person skilled in the art is given a wide range of possible variations.

LIST OF REFERENCE NUMBERS

1 Mixing and thawing device
2 Rocker drive
3 Bag holder
4 Substructure of 2
5 Rocker plate of 2
6 Rocker axis of 2
7 Bag
8 Base part of 3
9 Lid part of 3
10 Holding space of 3
11 Heating element
12 Lower part
13 Upper part
14 First intermediate space of 8
15 Second intermediate space of 9
16 Flow generator
17 Fluid flow
18 Condensate outlet
19 Gel pad

The invention claimed is:

1. A mixing and thawing device (1), comprising:
 a rocker drive (2) having a substructure (4) and a rocker plate (5) that is configured for pivoting relative to the substructure (4) about a rocker axis (6) at a programmable frequency and a programmable angle;
 a bag holder (3) having a base part (8) and a lid part (9) that enclose a holding space (10) for holding a bag (7), the holding space (10) being a heat-insulating closed chamber, the base part (8) of the bag holder (3) being fastened securely to the rocker plate (5);
 a heating element (11) being arranged in the base part (8)
 a first intermediate space (14) arranged between the bag (7) and the base part (8);
 a second intermediate space (15) arranged between the bag (7) and the lid part (9) and in fluidic communication with the first intermediate space; and
 at least one flow generator (16) for generating a circulating fluid flow (17) through the first and second intermediate spaces (14, 15) and on opposite sides of the bag (7).

2. The mixing and thawing device of claim 1, wherein the at least one flow generator is a fan and the fluid flow is an air stream.

3. The mixing and thawing device of claim 1, further comprising a lower part (12) arranged in the holding space (10) adjacent to the base part (8) and an upper part (13) arranged in the holding space (10) adjacent to the lid part (9).

4. The mixing and thawing device of claim 3, wherein the lower part (12) and the upper part (13) form a protective housing for the bag (7).

5. The mixing and thawing device of claim 1, wherein the base part (8) has one or more condensate outlets (18).

6. The mixing and thawing device of claim 3, wherein the bag (7) is fastened between the lower part (12) and the upper part (13) to prevent slippage.

7. The mixing and thawing device of claim 1, wherein the lid part (9) is removable from the base part (8).

8. The mixing and thawing device of claim 1, further comprising
a heat-conducting gel pad (19) arranged on the heating element (11) and facing the bag (7).

9. The mixing and thawing device of claim 8, wherein the gel pad (19) is flexible.

10. The mixing and thawing device of claim 8, wherein the heat-conducting gel pad regulates a temperature of the heating element.

11. The mixing and thawing device of claim 1, further comprising
one or more temperature sensor arranged within the bag holder (3).

12. The mixing and thawing device of claim 1, further comprising
a control and regulation device arranged within the rocker drive (2) for controlling and regulating a thawing and/or mixing that can be performed using the mixing and thawing device (1).

13. The mixing and thawing device of claim 12, wherein the control and regulation device is operable to operate the rocker drive (2) selectively for carrying out the mixing without heating or temperature-controlling the bag (7).

14. The mixing and thawing device of claim 3, wherein the lower part (12) and/or the upper part (13) are bowl-shaped.

* * * * *